United States Patent
Attariani et al.

(10) Patent No.: US 11,749,074 B2
(45) Date of Patent: Sep. 5, 2023

(54) RESCUE SUPPORT IN LARGE-SCALE EMERGENCY SITUATIONS

(71) Applicant: SONY CORPORATION, Tokyo (JP)

(72) Inventors: Mostafa Attariani, Malmö (SE); Karin Ahltin, Bjärred (SE); Sangxia Huang, Malmö (SE)

(73) Assignee: Sony Group Corporation, Tokyo (JP)

( * ) Notice: Subject to any disclaimer, the term of this patent is extended or adjusted under 35 U.S.C. 154(b) by 340 days.

(21) Appl. No.: 17/087,995

(22) Filed: Nov. 3, 2020

(65) Prior Publication Data
US 2021/0183214 A1    Jun. 17, 2021

(30) Foreign Application Priority Data
Dec. 13, 2019    (SE) .................................... 1951450-4

(51) Int. Cl.
*G08B 5/00* (2006.01)
*A61B 5/00* (2006.01)
(Continued)

(52) U.S. Cl.
CPC .............. *G08B 5/002* (2013.01); *A61B 5/746* (2013.01); *A62B 33/00* (2013.01); *B64C 39/024* (2013.01); *B64U 2101/20* (2023.01)

(58) Field of Classification Search
CPC ......... G08B 5/002; A61B 5/746; A62B 33/00; B64C 39/024; B64C 2201/122
(Continued)

(56) References Cited

U.S. PATENT DOCUMENTS 7,702,183 B1 * 4/2010 Johnson .................. G06T 7/277
382/294
10,203,701 B2    2/2019 Kurdi
(Continued)

FOREIGN PATENT DOCUMENTS

CN    104635243 A    5/2015
CN    106550054 A    3/2017
(Continued)

OTHER PUBLICATIONS

Extended European Search Report from corresponding European Application No. 20205414, dated May 3, 2021, 8 pages.
(Continued)

*Primary Examiner* — Kerri L McNally
*Assistant Examiner* — Thang D Tran
(74) *Attorney, Agent, or Firm* — Tucker Ellis LLP

(57) ABSTRACT

A method for rescue support involves distributing transponder devices to individuals in a geographic region and causing the transponder devices to be activated. If a large-scale emergency situation occurs, a fleet of unmanned aerial vehicles are operated within the geographic region to receive distress signals transmitted by the activated transponder devices. A computer system processes the distress signals to obtain detection data for the individuals, the detection data comprising a location of the respective transponder device and a health status of the respective individual. The computer system generates, based on the location and health status of the respective individual, a prioritization chart for the geographic region, the prioritization chart being indicative of one or more sub-regions to be prioritized for a rescue operation.

15 Claims, 6 Drawing Sheets

(51) Int. Cl.
*A62B 33/00* (2006.01)
*B64C 39/02* (2023.01)
*B64U 101/20* (2023.01)

(58) Field of Classification Search
USPC .................................................. 340/539.13
See application file for complete search history.

(56) References Cited

U.S. PATENT DOCUMENTS

| | | | | |
|---|---|---|---|---|
| 10,531,240 | B1* | 1/2020 | Sciancalepore | H04B 17/27 |
| 10,777,051 | B1* | 9/2020 | Kumar | B64D 47/02 |
| 2002/0119787 | A1* | 8/2002 | Hunzinger | H04W 76/19 |
| | | | | 455/452.2 |
| 2006/0149394 | A1* | 7/2006 | Patino | G08B 7/06 |
| | | | | 700/20 |
| 2006/0205412 | A1* | 9/2006 | Oh | H04W 16/02 |
| | | | | 455/450 |
| 2008/0122609 | A1* | 5/2008 | Mannisto | G08B 25/001 |
| | | | | 340/500 |
| 2016/0112853 | A1* | 4/2016 | Goossen | H04W 4/90 |
| | | | | 455/404.2 |
| 2016/0284038 | A1* | 9/2016 | Johnson | G16H 50/00 |
| 2016/0340006 | A1* | 11/2016 | Tang | B64C 39/024 |
| 2017/0084032 | A1* | 3/2017 | Zeng | B64D 47/08 |
| 2017/0088261 | A1* | 3/2017 | Sequeira | G05D 1/104 |
| 2017/0092109 | A1* | 3/2017 | Trundle | B60L 53/305 |
| 2017/0129603 | A1* | 5/2017 | Raptopoulos | G08G 5/0069 |
| 2017/0131727 | A1* | 5/2017 | Kurdi | G05D 1/0027 |
| 2017/0137124 | A1* | 5/2017 | Walker | A61B 5/08 |
| 2017/0256171 | A1* | 9/2017 | Thomas | G08G 5/0039 |
| 2017/0350959 | A1* | 12/2017 | Yaqub | G01S 3/40 |
| 2018/0027772 | A1* | 2/2018 | Gordon | G05D 1/104 |
| 2018/0039262 | A1* | 2/2018 | Fox | G08B 25/016 |
| 2018/0217249 | A1* | 8/2018 | La Salla | G06V 40/161 |
| 2018/0233016 | A1* | 8/2018 | Daniel | G16H 40/20 |
| 2018/0276351 | A1* | 9/2018 | Patton | G06F 21/6218 |
| 2018/0322749 | A1* | 11/2018 | Kempel | G05D 1/0094 |
| 2018/0327091 | A1* | 11/2018 | Burks | B64F 1/007 |
| 2019/0031342 | A1* | 1/2019 | Mitchell | G01S 17/42 |
| 2019/0164019 | A1* | 5/2019 | Djiofack | A61B 5/7267 |
| 2019/0286793 | A1* | 9/2019 | Patton | H04L 51/52 |
| 2020/0031438 | A1* | 1/2020 | Moses | B64C 25/54 |
| 2020/0256685 | A1* | 8/2020 | Kamphenkel | G01C 21/3407 |
| 2020/0372814 | A1* | 11/2020 | Bos | B64C 39/024 |
| 2020/0380404 | A1* | 12/2020 | Rakshit | G06N 20/00 |
| 2021/0129983 | A1* | 5/2021 | Ratti | B64B 1/44 |
| 2021/0269149 | A1* | 9/2021 | Culver | B64U 50/34 |
| 2021/0276675 | A1* | 9/2021 | Ökvist | B64C 39/024 |

FOREIGN PATENT DOCUMENTS

| | | |
|---|---|---|
| CN | 106598067 A | 4/2017 |
| KR | 101768624 B1 | 8/2017 |
| WO | 2017065347 A1 | 4/2017 |

OTHER PUBLICATIONS

Swedish Office Action with Search Report for corresponding Swedish Application No. 1951450-4, dated Oct. 14, 2020, 7 pages.
Dormehl, Luke, "Rescue drone can distinguish between survivors, victims in disaster zones", Digital Trends, published on Oct. 25, 2019, 4 pages.

* cited by examiner

US 11,749,074 B2

RESCUE SUPPORT IN LARGE-SCALE EMERGENCY SITUATIONS

RELATED APPLICATION DATA

This application claims the benefit of Swedish Patent Application No. 1951450-4, filed Dec. 13, 2019, the disclosure of which is incorporated herein by reference in its entirety.

TECHNICAL FIELD

The present disclosure relates generally to rescue operations in large-scale emergency situations and, in particular, to the use of unmanned aerial vehicles for providing situational awareness in such situations.

BACKGROUND ART

A large-scale emergency situation potentially involves several stranded, injured or dead persons and may be caused by a natural phenomenon such as a hurricane or tornado, an earthquake, a flooding, a tsunami, a volcano eruption, a landslide, an avalanche, a wildfire, etc., or an incidence such as a terrorist attack, an industrial accident, a plane crash, etc.

Search and rescue operations in these situations are hampered by a lack of overview and information. The victims may be entrapped and difficult to find for the rescue teams. Traditionally, search and rescue operations may be directed to areas identified by so-called structure triage, which pre-prioritize buildings or other structures for search teams. It is also common to initially deploy a reconnaissance (recon) team to perform a rapid visual check of a rescue environment to obtain information that may be used to develop a search plan and direct search and rescue operations. These measures are generally time-consuming, and time is critical for saving people in an emergency situation.

It has been proposed to deploy unmanned aerial vehicles, such as drones, to gather information to enhance situational awareness in emergency situations. US2018/0327091 discloses such a system in which a swarm of drones is deployed to monitor an affected area, for example by thermal sensors, and collectively relay information to remote dispatchers. However, given the chaotic nature of large-scale emergency situations, remote monitoring by drones is unlikely to provide sufficient information for an efficient search and rescue operation.

US2017/0092109 proposes to provide monitoring control units, each of which are associated with a respective property and configured to detect an emergency event based on data received from sensors installed throughout the property. A monitoring application server that receives an emergency event notification from one of the monitoring control units, transmits an instruction to launch one or more drones to the location associated with the emergency event notification.

There exists a need to provide support for more efficient use of resources when responding to large-scale emergency situations.

BRIEF SUMMARY

It is an objective to at least partly overcome one or more limitations of the prior art.

Another objective is to facilitate and/or improve prioritization of resources in responding to a large-scale emergency situation.

One or more of these objectives, as well as further objectives that may appear from the description below, are at least partly achieved by a system for rescue support, as well as a computer-readable medium, a device, and methods for rescue support according to the independent claims, embodiments thereof being defined by the dependent claims.

A first aspect of the present disclosure is a system for rescue support. The system comprises: a fleet of unmanned aerial vehicles for deployment within a geographic region, the unmanned aerial vehicles being configured to receive distress signals transmitted by transponder devices worn or carried by individuals in the geographic region subsequent to a large-scale emergency situation; and a computer system. The computer system is configured to: process the distress signals to obtain detection data for the individuals, the detection data comprising a location of a respective transponder device among the transponder devices and a health status of a respective individual among the individuals; and generate, based on the location and health status, a prioritization chart for the geographic region, the prioritization chart being indicative of one or more sub-regions to be prioritized for a rescue operation.

A second aspect of the present disclosure is a computer-implemented method for rescue support. The method comprises: obtaining detection data representative of distress signals that are transmitted subsequent to a large-scale emergency situation by transponder devices worn or carried by individuals in a geographic region and received by unmanned aerial vehicles in a fleet of unmanned aerial vehicles deployed within the geographic region, the detection data comprising a location of a respective transponder device among the transponder devices and a health status of a respective individual among the individuals; and generating, based on the location of and health status, a prioritization chart for the geographic region, the prioritization chart being indicative of one or more sub-regions to be prioritized for a rescue operation.

Any embodiment of the first aspect described herein may be adapted as an embodiment of the second aspect.

A third aspect of the present disclosure is a computer-readable medium comprising computer instructions which, when executed by a processing system, cause the processing system to perform the method of the second aspect or any of its embodiments.

A fourth aspect of the present disclosure is a device comprising logic configured to control the device to perform the method of the second aspect or any of its embodiments.

A fifth aspect of the present disclosure is a method for rescue support. The method comprises: distributing transponder devices to individuals in a geographic region; causing the transponder devices to be activated; controlling a fleet of unmanned aerial vehicles operable within the geographic region to receive distress signals transmitted by the transponder devices subsequent to a large-scale emergency situation in the geographic region, and operating a computer system to: process the distress signals to obtain detection data for the individuals, the detection data comprising a location of a respective transponder device among the transponder devices and a health status of a respective individual among the individuals, and generate, based on the location and health status of the respective individual, a prioritization chart for the geographic region, the prioritization chart being indicative of one or more sub-regions to be prioritized for a rescue operation.

The foregoing aspects ensure availability of both health status and location of individuals in a geographic region that is struck by a large-scale emergency situation. The combination of location and health status enables the prioritization chart to be generated to properly represent casualties and/or individuals in need of help and thereby enables more efficient use of resources when responding to large-scale emergency situations.

Still other objectives and aspects, as well as features, embodiments and technical effects will appear from the following detailed description, from the attached claims as well as from the drawings.

BRIEF DESCRIPTION OF DRAWINGS

Embodiments will now be described in more detail with reference to the accompanying schematic drawings.

DETAILED DESCRIPTION OF EXAMPLE EMBODIMENTS

Figure 1:
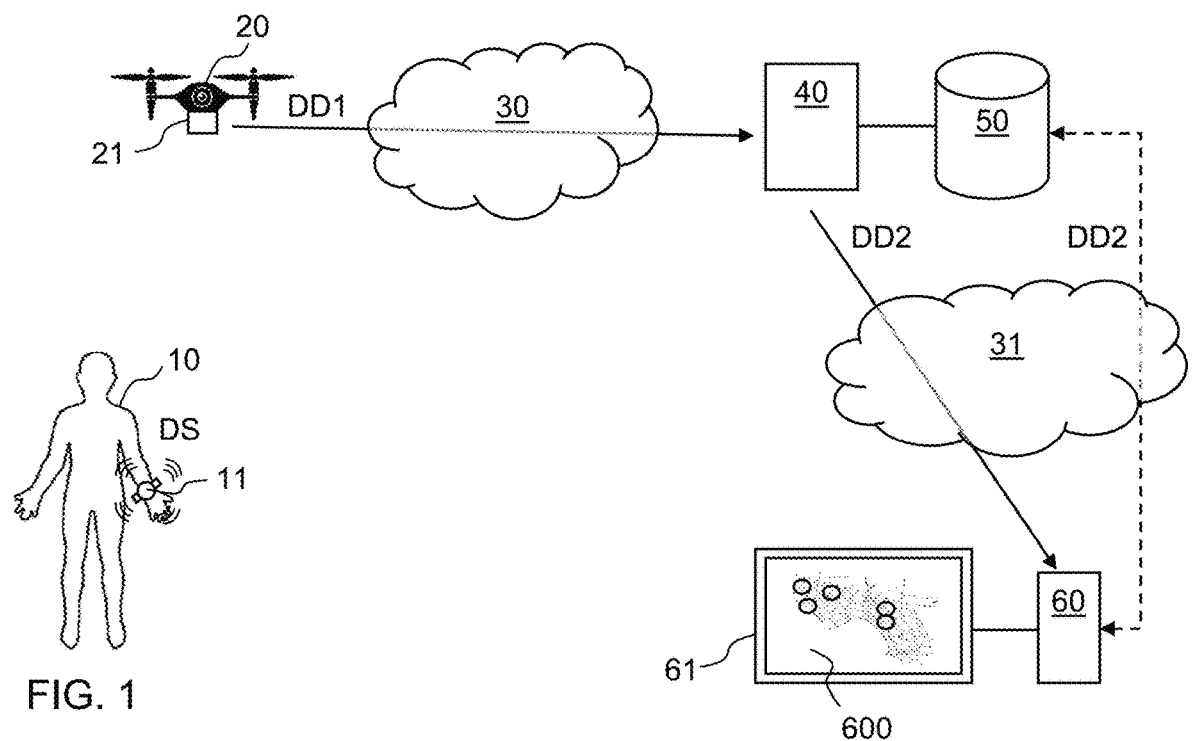
FIG. 1 is an overview of an example system for rescue support.

Embodiments will now be described more fully hereinafter with reference to the accompanying drawings, in which some, but not all, embodiments are shown. Indeed, the subject of the present disclosure may be embodied in many different forms and should not be construed as limited to the embodiments set forth herein; rather, these embodiments are provided so that this disclosure may satisfy applicable legal requirements.

Also, it will be understood that, where possible, any of the advantages, features, functions, devices, and/or operational aspects of any of the embodiments described and/or contemplated herein may be included in any of the other embodiments described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments. The term "compute", and derivatives thereof, is used in its conventional meaning and may be seen to involve performing a calculation involving one or more mathematical operations to produce a result, for example by use of a computer.

As used herein, the terms "multiple", "plural" and "plurality" are intended to imply provision of two or more elements, whereas the term a "set" of elements is intended to imply a provision of one or more elements. The term "and/or" includes any and all combinations of one or more of the associated listed elements.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present disclosure.

Well-known functions or constructions may not be described in detail for brevity and/or clarity. Unless otherwise defined, all terms (including technical and scientific terms) used herein have the same meaning as commonly understood by one of ordinary skill in the art to which this disclosure belongs.

Like numerals refer to like elements throughout.

Before describing embodiments in more detail, a few definitions will be given.

As used herein, "large-scale emergency situation" refers any situation that may potentially cause harm to a large number of individuals, including but not limited to situations caused by natural phenomena, accidents or deliberate acts, for example as discussed in the Background section.

As used herein, "unmanned aerial vehicle" (UAV) refers to an aircraft controlled by an onboard automated control system, a ground-based control system or by a ground-based human pilot. Such an aircraft is also known as "uncrewed aerial vehicle" or drone.

Embodiments relate to a technique for supporting rescue operations in large-scale emergency situations. The purpose of a rescue operation is to help and eventually evacuate individuals that are in an actual or potentially dangerous situation. Depending on the state and local environment of the respective individual and/or the future development of the situation, a short time to rescue may be of essence. However, it is challenging to coordinate the rescue efforts in a large-scale emergency situation. Many individuals may be hidden from view and the health status of the respective individual is unknown. The technique described herein for supporting rescue operations may serve to facilitate coordination of rescue efforts and significantly shorten the time to locate individuals that are stranded, distressed, injured or otherwise in need of help.

Embodiments of the technique will be described with reference to FIG. 1, which schematically illustrates an example system for rescue support. In the illustrated example, the system comprises transponder devices ("transponders") 11 (one shown), UAVs ("drones") 20 (one shown), processing devices 40, 60 and a display device 61. The transponder 11 is worn or otherwise carried by an individual 10 who is in a geographic region that is subject to a large-scale emergency situation. The transponder 11 has been activated to broadcast a distress signal DS, which comprises health data indicative of the health status of the individual. The health data may enable discrimination between living and dead individuals. In some embodiments, the health data may additionally enable classification of living individuals into different health categories. The respective drone 20 includes a control device ("controller") 21 which is configured to intercept the distress signal DS and to generate and transmit first data DD1 to a first processing device 40 over a first network 30. The first data DD1 is generated based on the distress signal DS and is indicative of the location of the transponder 11 and the health status of the individual 10. The first processing device 40 processes the first data DD1 to generate second data DD2 and may provide the second data DD2 for storage in a database 50. The second data DD2 may be a collection of first data DD1 from different drones 20 and/or contain a refinement of the first data DD1, for example with respect to location or health status. The second processing device 60 obtains the second data DD2 over a second network 31, from the first processing device 40 and/or by retrieval from the database 50 (cf. dashed line in FIG. 1). The second processing device 60 operates the display device 61, which may be located at a rescue coordination center for the geographic region, to display supporting data for the rescue operation. The supporting data comprises a prioritization chart 600 that indicates one or more sub-regions to be prioritized for the rescue operation in the geographic region. The prioritization chart 600 may be generated by the first processing device 40 and/or the second processing device 60 based on the data collected by the drones in the geographic region. The prioritization chart 600 thereby provides a current status overview of the geographic region, and the system may be configured to present the prioritization chart 600 in real-time or near real-time. Further, the prioritization chart 600 may be updated, continuously or intermittently, based on data collected by the drones 20.

Figure 3A:
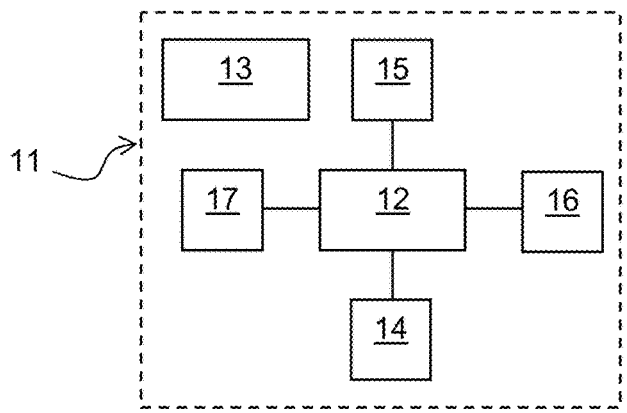
FIGS. 3A-3B are block diagrams of a personal transponder and a drone controller, respectively.

FIG. 3A is a block diagram of an example transponder 11 which is worn or otherwise carried by an individual. The transponder 11 comprises a processor 12, a power source 13, a signal transmitter 14, a sensor arrangement 15, an on/off switch 16, and an indicator 17. The power source 13 may comprise a battery or a fuel cell for supplying power to components such as the processor 12, the transmitter 14 and the indicator 17. The transmitter 14 is configured to transmit a wireless signal in any suitable frequency range, continuously or at intervals. The wireless signal may be a radio signal. The wireless signal may be capable of penetrating obstacles such as building material. The transmitter 14 may be configured to encode data in the wireless signal in accordance with any standardized or proprietary communication protocol. In some embodiments, the transmitter 14 is configured for short-range or medium-range communication, for example by a wireless standard such as Bluetooth, BLE, Wi-Fi, Wi-SUN, EnOcean, or UWB. The sensor arrangement 15 may comprise one or more sensors that are integrated in or otherwise associated with the transponder 11. The sensor arrangement 15 is configured to sense parameter data representative of the individual that carries the transponder 11. The parameter data may comprise one or more physiological parameters such as heart rate ("pulse"), body temperature, blood pressure or breathing rate. Alternatively or additionally, the parameter data may represent movement of the individual. Non-limiting examples of sensors that may be included in the sensor arrangement 15 comprise accelerometers, gyroscopes, magnetometers, altimeters, pedometers, vibration sensors, blood pressure sensors, skin temperature sensors, heart rate sensors, sweat sensors, moisture sensors, breathing rate sensors, and bioelectric current sensors. The processor 12 is operable to acquire the parameter data from the sensor arrangement 15 and cause the transmitter 14 to broadcast the above-mentioned distress signal DS containing the parameter data, or data derived therefrom. The on/off switch 16 is connected to the processor 12, thereby allowing the transponder 11 to be manually activated. The indicator 17, for example comprising one or more LEDs or lamps, may be arranged to indicate when the transponder 11 is activated and/or when the transmitter 11 is operated to broadcast the distress signal DS.

In some embodiments, the transponder 11 is a simple and inexpensive electronic device. For example, the transponder 11 may be a wearable electronic device. In some embodiments, the transponder 11 is included in a mobile phone or a smart watch. In some embodiments, the transponder 11 is configured to be activated manually by the individual 10, for example via the on/off switch 16. In some embodiments, the transponder 11 is configured to be activated automatically when attached to the individual 10, e.g. based on a signal from the sensor arrangement 15. In some embodiments, the transponder 11 is configured to be remotely activated, for example by a signal received by a signal receiver (not shown) in the transponder 11. In some embodiments, the transponder 11 is configured to be power-efficient. In some embodiments, the transponder 11 is operable in an ultra-low power state when not activated and a low power state when activated.

Figure 3B:
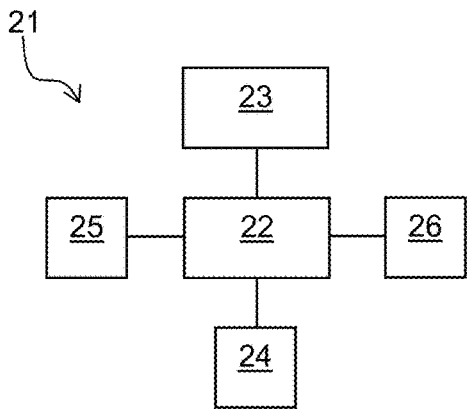

FIG. 3B is a block diagram of an example controller 21 for installation on a drone. The controller 21 comprises a processor 22, a GNNS receiver 23, a signal receiver 24, a signal transceiver 25, and a sensor arrangement 26. The controller 21 may be connected to or part of a main controller for the drone 20. The processor 22 operates the controller 21. The controller 21 may be configured to determine global positions of the drone 20 based on position data from the GNNS receiver 23 by use of a satellite navigation system, including but not limited to GPS, QZSS, GLONASS, NAVIC, BDS, and optionally in combination with one or more further positioning techniques such as INS (Inertial Navigation System) and/or SLAM (Simultaneous Localization and Mapping), which are well-known to the person skilled in the art. The signal receiver 24 is configured to receive the wireless signals transmitted by the transponder 11. The signal transceiver 25 is configured to wirelessly communicate with the first processing device 40 over the first network 30 (FIG. 1), in accordance with any standardized or proprietary communication protocol. However, since mobile and other ground-based communication networks may be unavailable in an emergency situation, the signal transceiver 25 may be configured with a radio layer with a long signal range, for example at least 0.5 km, or at least 5 or 10 km. The signal transceiver 25 may further be operable for non-cellular communication. In some embodiments, the signal transceiver 25 supports satellite communication or LPWAN (Low-Power Wide-Area Networks) communication, for example in accordance with LoRa, Sigfox, RPMA (Random Phase Multiple Access), Weightless, etc. The sensor arrangement 26 may include one or more environmental sensors configured to collect information about the local environment. By the environmental sensor(s), the sensor arrangement 26 may generate environment data representative of the surroundings of the drone 20. The environmental sensor(s) may include one or more imaging devices, for example a digital camera, a thermographic camera, a multispectral camera, a LIDAR sensor, etc., and/or one or more ambient sensors, such as temperature sensor, pressure sensor, sound detector, weather sensor, wind sensor (speed, direction), humidity sensor, dew point sensor, substance sensor (gas, chemicals), radioactivity sensor, etc. Although not shown in FIG. 3B, the controller 21 may further comprise a spotlight to illuminate the local environment, for example the terrain beneath the drone. The sensor arrangement 26 may also include one or more orientation sensors, such as one or more accelerometers, gyroscopes, magnetometers, altimeters, etc. The controller 21 may be configured to determine the current orientation of the drone 20 based on data from the orientation sensor(s). For example, the current orientation may be given by any combination of pitch, roll and yaw.

Reverting to FIG. 1, the second network 31 may be any suitable LAN, MAN or WAN, or combination thereof. If the first processing device 40 is located sufficiently far from the emergency situation, the second network 31 may be or comprise an existing wireless cellular network, for example compliant with the 3GPP standard and/or a land-based communication network.

Figure 4:
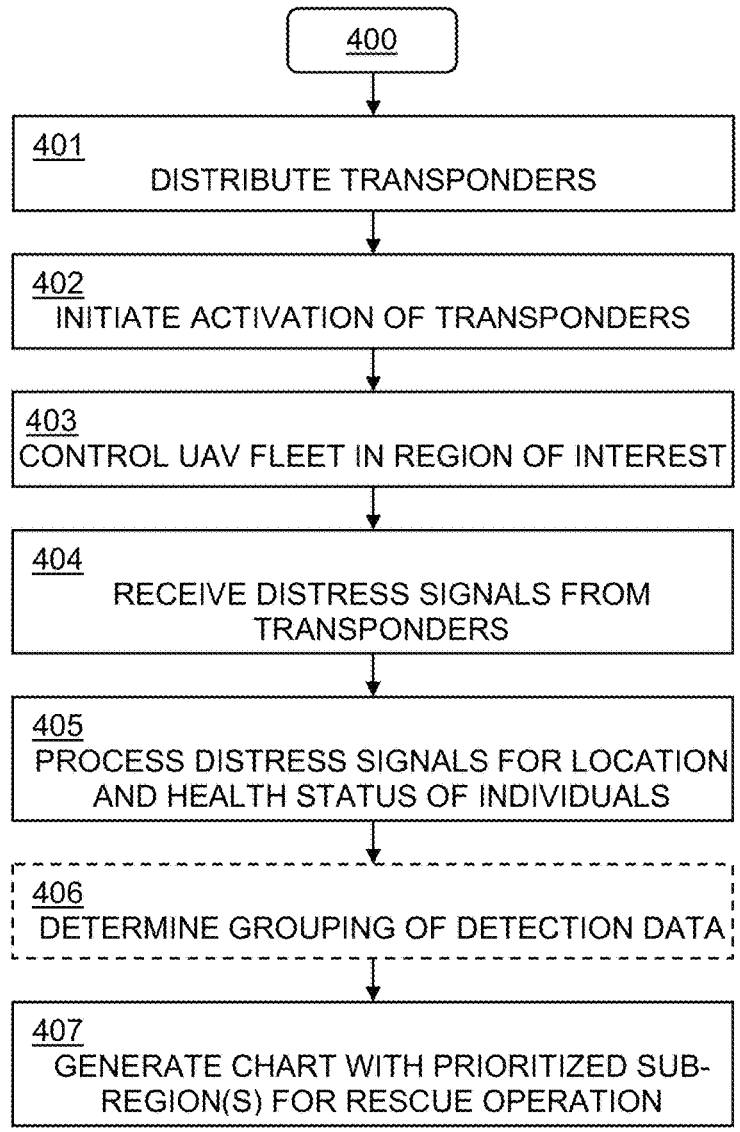
FIG. 4 is a flow chart of method for rescue support.

FIG. 4 is a flow chart of an overall method 400 for rescue support in accordance with an embodiment, which method may be implemented within the system of FIG. 1.

In step 401, transponders 11 are distributed to individuals 10 within a geographic region in anticipation of a large-scale emergency situation. For example, the transponders 11 may be distributed within a region that is known, predicted or deemed likely to suffer from a natural disaster, such as a hurricane, a flooding, an avalanche, an earthquake, a tsunami, etc. Transponders 11 may also be distributed within a region deemed likely to be targeted by a terrorist attack or a region with industries that would cause large-scale devastation in the event of a major malfunction or accident, for example a chemical plant, an oil refinery or a nuclear power plant. In another example, transponders may be preemptively distributed to all individuals within a country, state, province, county, city etc. In step 402, activation of the transponders 11 is initiated, for example, in response to an emergency situation. When activated, the respective transponder 11 operates its transmitter 14 to transmit the distress signal. Step 402 may be performed before step 401, so that the transponders 11 are active when distributed. Alternatively, step 402 may be performed in anticipation of the emergency situation. If the transponders 11 are configured to be manually activated, step 402 may involve distributing, by any communication channel, an appeal to the people in the geographic region to activate their transponders. If the transponders 11 are configured to be activated automatically when attached to the individuals, step 402 may be inherent to step 401. If the transponders 11 comprise a signal receiver and are configured for remote activation, step 402 may involve transmitting an activation signal to the transponders 11. It is also conceivable that the transponders 11 are being activated, manually or remotely, during the emergency situation.

Figure 2:
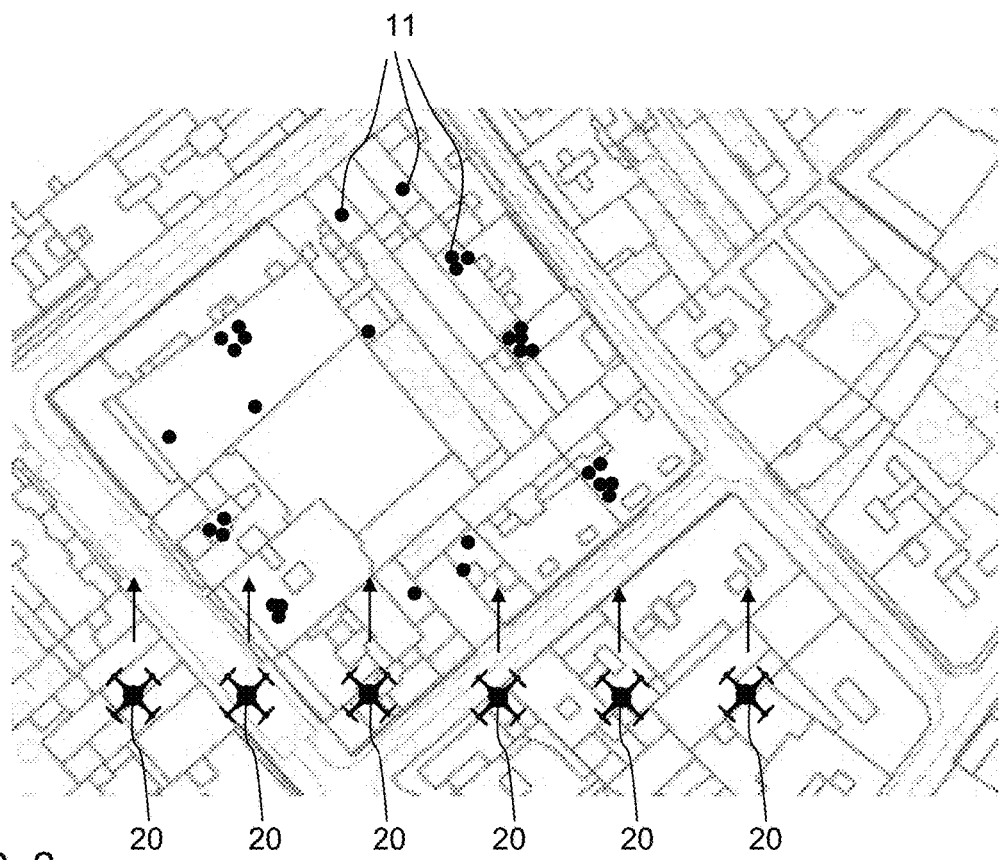
FIG. 2 is a top plan view of a fleet to drones monitoring a region affected by a large-scale emergency situation.

Steps 403-407 are performed during the emergency situation. In step 403, a fleet or swarm of drones 20 are operated to co-operatively work together to cover a region of interest, which may be the geographic region or part thereof. The drones 20 may be actively dispatched to the region of interest during or before the emergency situation or they may be already present in the region of interest for another purpose. In step 404, while moving within the region of interest, the drones 20 are operated to intercept (receive) distress signals from transponders 11. FIG. 2 is a top plan view of a plurality of drones 20 that are operated to fly over an area in search for distress signals from transponders 11 (black dots). In some scenarios, a swarm of drones 20 may be programmed into a bird-like formation cutting through the sky. In other scenarios, a smaller number of drones 20 may take individual paths to work together to scan an area. For example, a swarm of drones 20 may share a common map of a terrain, communicating to each other the position already monitored, and choose (in real-time or near real-time) the next position to be visited.

In step 405, the respective distress signal is processed for determination of detection data comprising the location of the transponder 11 and the health status of the individual carrying the transponder 11. The health status may be determined based on one or more physiological parameters that are measured (cf. sensor arrangement 15 in FIG. 3A) and may be embedded in the distress signal by the transponder 11. In one embodiment, the location is measured and embedded in the distress signal by the transponder 11, for example by use of an integrated GNNS sensor. In another embodiment, which eliminates the need for a GNNS sensor in the transponder 14 and thus enables the transponder 14 to have low power consumption, cost and complexity, the location is determined based on position parameters measured by the drone 20 that intercepts the distress signal. The position parameters may include a global position of the drone 20 and at least one of a distance and/or a direction from the drone 20 to the transponder 11. The global position of the drone 20 may be given by a GNNS receiver (cf. 23 in FIG. 3B) on the drone 20.

In the example of FIG. 1, step 405 may be performed by the controller 21, and the first data DD1 may comprise a combination of location and health status for each unique distress signal DS. In one embodiment, the distress signal DS comprises a transponder identifier (TID) which is unique to the originating transponder 11, and step 405 comprises extracting the TID from the respective distress signal and determining the location and health status for each unique TID. The TID enables discrimination between transponders 11 and ensures consistent data collection. In the example of FIG. 1, the TID may be included in the first data DD1 in association with the location and health status. This will enable the first processing device 40, when receiving first data DD1 from different drones 20, to detect data sets originating from the same transponder 11. In one embodiment, one data set may be selected from such data sets. In another embodiment, the data sets may be merged, for example by computing an average location and/or health status.

Step 407 generates the prioritization chart 600 with prioritized sub-region(s) for the rescue operation. The prioritization chart 600 is generated based on the detection data determined in step 405 for transponders within the geographic region. Examples of prioritization charts will be presented further below with reference to FIG. 6.

Figure 5A:
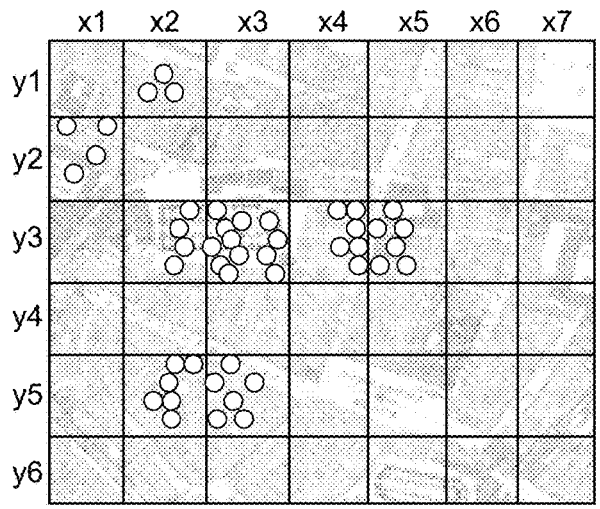
FIGS. 5A-5B are examples of spatial grouping of detection data gathered by drones.
Figure 5B:
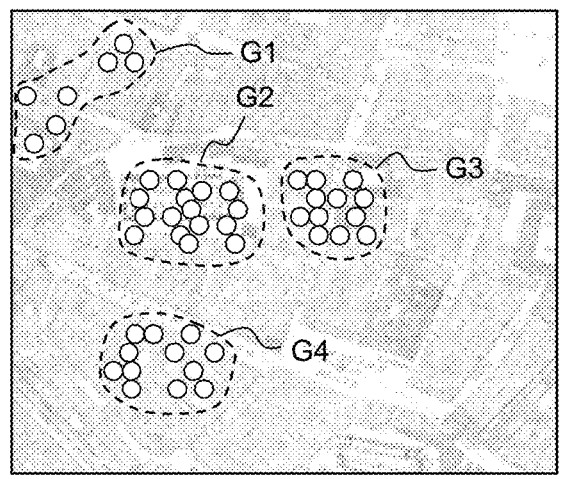

As indicated in FIG. 4, the method may comprise a step 406 that determines a grouping of the detection data as a function of at least the location of the respective transponder 11, resulting in a plurality of groups. In one embodiment of step 406, shown in FIG. 5A, the detection data is mapped, by its content of locations, to a fixed arrangement of cells or sections within the geographic region. In one example, the cells are defined by a predefined grid. In FIG. 5A, the grid comprises quadrilateral cells which are uniquely identified by a pair of x-y coordinates, and the locations are represented by white dots. In another embodiment of step 406, shown in FIG. 5B, a clustering function is operated on the detection data to identify clusters of locations. The clustering function may be a density-based clustering function. Any such clustering function may be used, including but not limited to DBScan, OPTICS, mean-shift, etc. In FIG. 5B, clusters a delimited by dashed lines and designated by G1-G4, and the locations are represented by white dots. Step 406 may further determine the density of individuals in the respective group.

Step 406 may further factor in the health status when determining the grouping. In one embodiment, step 406 identifies selected individuals based on the health status and determines the grouping for the selected individuals. In one example, individuals indicated as dead by the health status are excluded, leaving all living individuals as selected individuals. In another example, if the health status enables classification of living individuals into different health categories, the selected individuals may belong to one or more selected health categories. In a further alternative, the health status may be analyzed after the grouping, for example to exclude dead individuals and/or individuals in one or more health categories before determining the density of the respective group.

Figure 6:
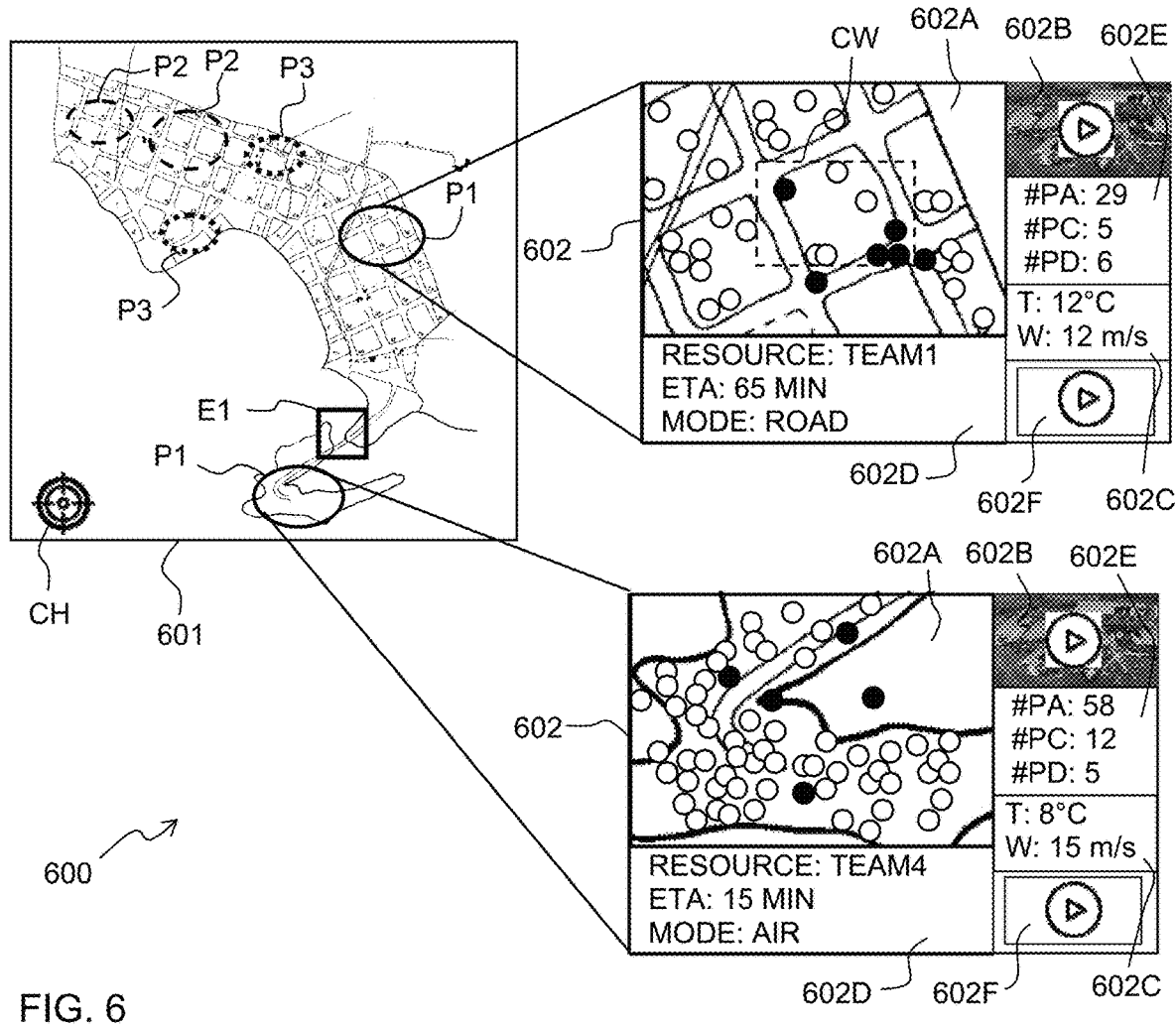
FIG. 6 shows a prioritization chart generated for a region affected by a large-scale emergency situation.

FIG. 6 shows an example of a prioritization chart 600 generated by step 407. The chart 600 comprises a graphical overview ("graphics") 601 of the geographic region, for example a map, a 3D representation, or a satellite image (real-time or pre-recorded). Sub-regions of one or more priorities are indicated on the chart. In FIG. 6, the chart 600 indicates sub-regions assigned three different priorities, with sub-regions P1 having top priority, sub-regions P2 having high priority and sub-regions P3 having medium priority. Step 407 may assign any number of different priorities and determine sub-regions P1-P3 in any size and shape. The different priorities may be visually separated on the chart 600. In one embodiment, the sub-regions P1-P3 are indicated by a choropleth map, in which the graphics 601 is shaded or patterned in proportion to the priority value. In one example, the choropleth map implements a color coding to produce a so-called heat map. Step 407 may generate the chart 600 based on the plurality of groups from step 406. For example, a sub-region may be equal to or include one or more of the groups. In one embodiment, step 407 assigns a priority value to the respective group, for example based on its density of individuals and/or the health status of the included individuals and indicates the sub-regions in the chart 600 based on the priority values of the groups. In one example, step 407 includes, in one or more sub-regions, group(s) with the highest density of individuals.

In some embodiments, step 407 generates the chart 600 to enable a user to zoom in on the graphics 601 and/or be presented with further information about a sub-region or part thereof. An example is shown in FIG. 6, where the chart 600 comprises highlight panels 602 with enlarged graphics 602A. The highlight panels 602 may be fixed or shown on command.

In some embodiments, step 407 generates the chart 600 based on the environment data from the above-mentioned environmental sensor(s) in the sensor arrangement on the respective drone (cf. 26 in FIG. 3B). In some embodiments, step 407 includes at least part of environment data detected by one or more drones in chart 600, for example images, temperature, pressure, gas content, humidity, sound, etc. An example is shown in FIG. 6, where the chart 600 comprises sub-panels 602B providing access to image(s) or video recorded by the imaging device on a respective drone and possibly audio recorded by a sound detector. Further, sub-panels 602C show temperature and wind speed detected by ambient sensors on a respective drone.

In some embodiments, step 407 determines the prioritized sub-region(s) as a function of the environment data. For example, step 407 may predict a local worsening of the emergency situation based on the environment data, for example images recorded by one or more drones. For example, step 407 may detect a fire that calls for a high priority of a sub-region or a group.

In some embodiments, step 407 processes the environment data, such as one or more images, from one or more drones to determine an infrastructure status within the geographic region. The infrastructure status may represent the current condition of roads, bridges, airports, seaports, etc. Step 407 may further indicate the infrastructure status on the chart 600. In FIG. 6, a demolished bridge is indicated by square E1 in the graphics 601. In some embodiments, step 407 determines the prioritized sub-region(s) as a function of the infrastructure status. For example, as indicated in FIG. 6, sub-region P1 may be set to top priority since the bridge is demolished and individuals are trapped on an island.

In some embodiments, step 407 determines, based on the infrastructure status, an estimated time of arrival to the sub-region(s) for one or more rescue teams located at a respective current location in relation to the geographic region, and includes the estimated time of arrival in the chart 600. Step 407 may be performed for different modes of transport that are available to the respective rescue team. In FIG. 6, the chart 600 comprises sub-panels 602D indicating a rescue team ("resource") and an estimated time of arrival ("ETA") for the rescue team to a respective sub-region by use a specified mode of transport ("mode"). Step 407 may determine the current location of the respective rescue team from location signals transmitted by rescue teams, or from input data provided by an operator at the rescue coordination center.

In some embodiments, step 407 indicates, in the chart 600, the current location of one or more rescue teams in relation to the geographic region. It is understood that the current location may be within or outside the geographic region.

In some embodiments, step 407 selects, based on the infrastructure status, one or more candidate rescue teams among a set of available rescue teams, and indicates the selected candidate rescue team(s) in the chart 600. The candidate rescue teams may be selected based on estimated time of arrival, availability of rescue equipment in relation the health status of individuals in the respective sub-region, etc. In FIG. 6, the resources indicated in sub-panels 602D may be such selected candidate teams.

In some embodiments, step 407 selects, based on the infrastructure status, a mode of transport among a set of available modes of transport for at least one rescue team, and indicates the selected mode of transport in the chart 600. In FIG. 6, the modes indicated in sub-panels 602D may be such selected modes.

In some embodiments, step 407 obtains rescue status data indicative of locations visited by one or more operative rescue teams, and indicates the locations visited on the chart 600. Step 407 may determine the rescue status data from status signals transmitted by the operative rescue teams or from input data provided by an operator at the rescue coordination center.

In some embodiments, step 407 determines, based on the infrastructure status, a transportation route for a rescue team to the sub-region(s), and indicates the transportation route in the chart 600. Further, step 407 may cause the determined route to be transmitted to the rescue team, subject to approval by an operator at the rescue coordination center, to synchronize the activity of the rescue team with the decisions taken at the rescue coordination center.

In some embodiments, step 407 includes indicators of individuals or ensembles of individuals in the chart 600. The indicators may designate the location of the individuals/ensembles, and optionally the health status. In FIG. 6, the locations of living and dead individuals are indicated by white and black dots, respectively, in the enlarged graphics 602A.

In some embodiments, step 407 generates, based on the detection data (location and health status), a count of living individuals in the sub-region(s) and includes the count in the chart 600. In FIG. 6, the chart 600 includes sub-panels 602E that designate the number of living individuals (#PA), the number of individuals with critical health status (#PC), and the number of dead individuals (#PD) in the respective sub-region P1.

In some embodiments, step 407 provides, via the chart 600, real-time access to the controller 21 on a drone 20 in the fleet of drones. Thus, step 407 may establish real-time communication with the signal transceiver 25 of the controller 21 on the drone 20 (FIG. 3B) and transmit control signals for the processor 22 of the controller 21. In some embodiments, the access to the controller 21 comprises an interface on the chart 600 for controlling the drone to a selected location in the geographic region. In FIG. 6, the interface is represented by a crosshair icon CH which is moveable over the graphics 601, by an operator at the rescue coordination center, to control a drone 20 to the specific location. In some embodiments, the access to the controller 21 comprises an interface on the chart 600 for real-time access to the sensor arrangement on a drone 20. In FIG. 6, the chart 600 comprises sub-panels 602F providing real-time access to image(s) or video recorded by the imaging device on a drone and possibly audio recorded by a sound detector. In some embodiments, step 407 determines and indicates the current field of view of the imaging device in relation to the geographic region. In FIG. 6, the current field of view is represented by a dashed rectangle CW overlaid on the enlarged graphics 602A.

Figure 7:
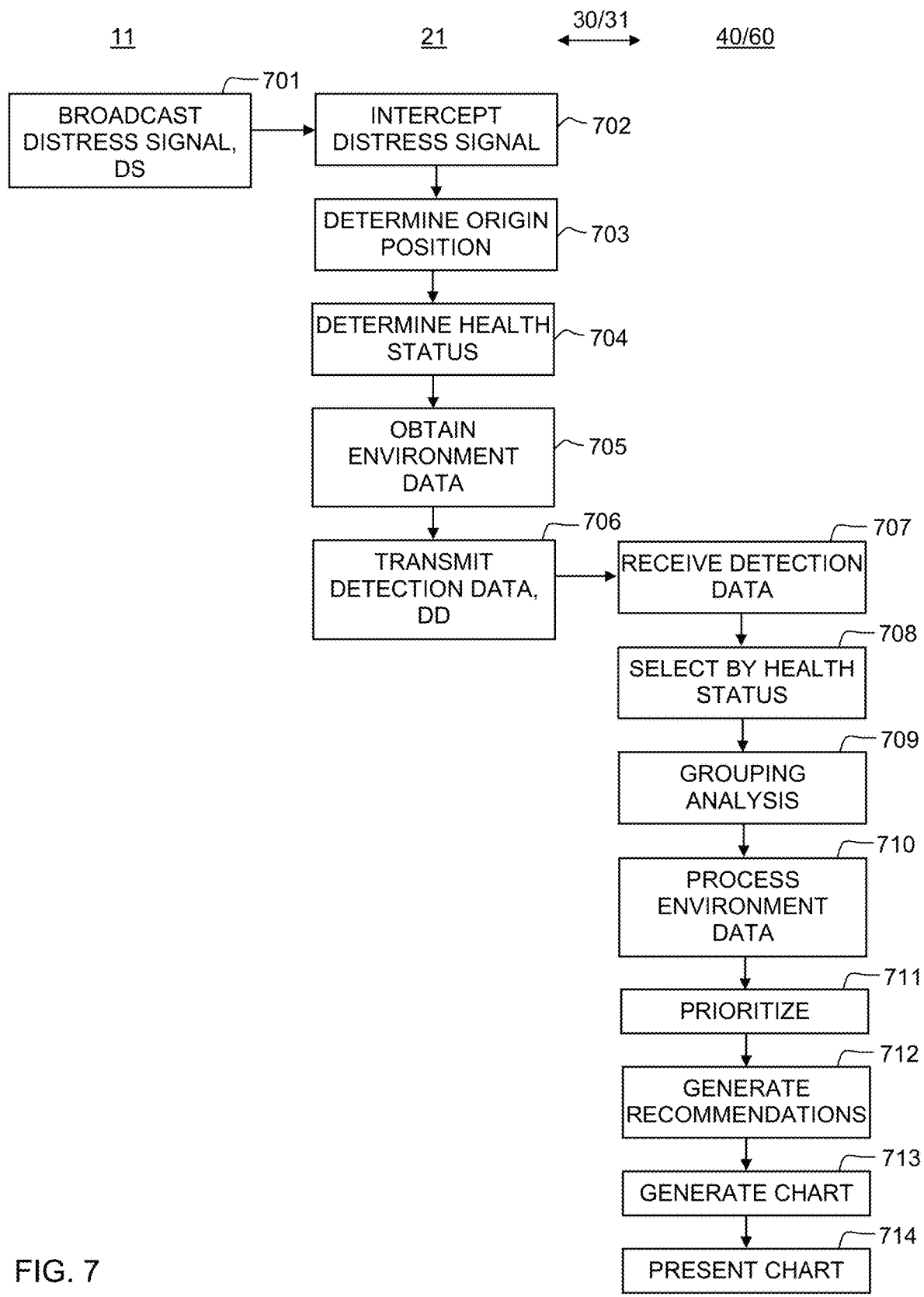
FIG. 7 is a flow chart of a method for rescue support.

FIG. 7 is a flowchart on an embodiment of a method performed in the system of FIG. 1. The method is distributed between the transponders 11 (one shown), the controllers 21 (one shown), and a processing system comprising one or both of the processing devices 40, 60. In step 701, the transponder 11 broadcasts the distress signal DS. In step 702, the distress signal DS is intercepted by the controller 21.

In step 702, the controller 21 may also extract the above-mentioned TID from the distress signal and compare the TID with previous TIDs extracted within a time period. If the TID has been previously extracted within the time period, steps 703-706 may be omitted. In a variant, step 703 is performed on the distress signal that comprises such a subsequent TID, and steps 704-706 may be performed if the determined position of origin (see below) differs significantly between the subsequent TID and the previous TID. In step 702, a transmitter in the controller 21 may also transmit a confirmation signal for receipt by a receiver in the transponder 11, the confirmation signal causing the processor 12 (FIG. 3A) to activate the indicator 17 to signal that the distress signal has been intercepted.

In step 703, the controller 21 determines the position of origin for the distress signal DS, for example by extracting position data embedded by the transponder 11 in the distress signal or by processing the distress signal (cf. FIG. 8 below). The position of origin designates the location of the transponder 11 and thus an approximate location of the individual carrying the transponder 11. In step 704, the controller 21 determines the health status of the individual based on parameter data embedded in the distress signal by the transponder 11. In step 705, the controller 21 obtains environment data from its sensor arrangement 25. In step 706, the controller 21 generates detection data DD which comprises a combination of TID, location and health status from one or more distress signals, as well as the environment data, and transmits the detection data DD to the processing system 40/60, which performs steps 707-714 on detection data DD received from a plurality of drones located within the geographic region. The controller 21 may include further parameters in the detection data, such as a unique identifier of the drone, a current global position of the drone, a current timestamp, etc.

In step 707, the detection data DD is received and processed for extraction of the location, health status and environment data. In step 707, combinations of location and health status from the same transponder 11 may be identified based on the TID and processed as described hereinabove. In step 708, the extracted data from step 707 may be processed as a function of health status, for example to determine locations associated with living individuals and/or individuals of a specific health category. In step 709, a grouping analysis may be performed for the locations in the detection data from step 708 to determine one or more spatially-coherent groups of individuals and a density of individuals for each group. In step 710, the environment data may be processed, for example for determination of an infrastructure status. In step 711, a prioritization may be performed among the groups determined by step 709, for example based on the density of individuals, and possibly in view of the infrastructure status, health status or any other data, for example as described with reference to FIG. 6. Step 711 results in the sub-regions to be indicated on the prioritization chart 600. In step 712, recommendations for the rescue operation may be generated by based on detection data. Such recommendations may comprise the above-mentioned mode of transport, candidate rescue team(s), transportation route, estimated-time of arrival, etc. The prioritization chart is generated (step 713) and presented (step 714) on the display device 61.

Figures 8A, 8B, 8C:
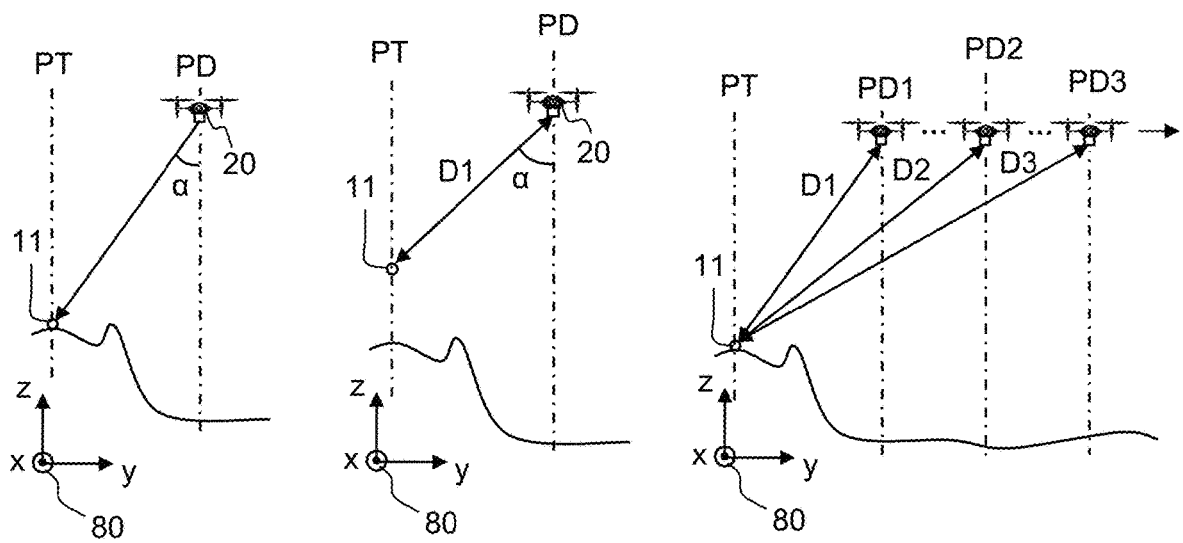
FIGS. 8A-8C are schematic side views of a drone in relation to a transponder.

To reduce complexity and cost of the transponder 11, the location of the respective transponder 11 may be computed externally of the transponder 11, for example by step 405 and step 703, based on the distress signal DS as received by the controller 21 on the drone 20 irrespective of the content of the distress signal. Various example embodiments for such computations are illustrated in FIGS. 8A-8C. In FIG. 8A, the distress signal is processed to determine the angle-of-incidence a at the signal receiver 24 (FIG. 3B). Given that the current drone position PD in a fixed coordinate system 80 is known, for example a GNNS position, and that the topography of the terrain around PD is known or estimated, for example from the environmental sensors on the drone, the location PT of the transponder 11 in the coordinate system 80 may be computed by intersecting the angle-of-incidence with the topography. In FIG. 8B, the distress signal is processed to determine both the angle-of-incidence a and the distance D1 from the drone 20 to the transponder 11. The distance D1 may be determined based on the signal strength at the signal receiver 24 (FIG. 3). By combining the angle-of-incidence a, the distance D1 and the current drone position PD, the location PT of the transponder 11 in the coordinate system 80 may be computed irrespective of topography. In FIG. 8C, the distress signal is processed to determine the distance D1, D2, D3 from the drone 20 to the transponder 11 at three or more different drone positions PD1, PD2, PD3, which may be attained by one drone at three or more time points (as shown) and/or by different drones. By combining the distances D1-D3 and the drone positions PD1-PD3, the location PT of the transponder 11 in the coordinate system 80 may be computed irrespective of topography. Further alternatives are conceivable, as understood by the skilled person. The accuracy of the location PT, when determined based on angle-of-incidence, may be improved by also accounting for the current orientation of the drone 20. As noted above, the controller 21 may determine the current orientation based on data from one or more orientation sensors on the drone 20.

Figure 9A:
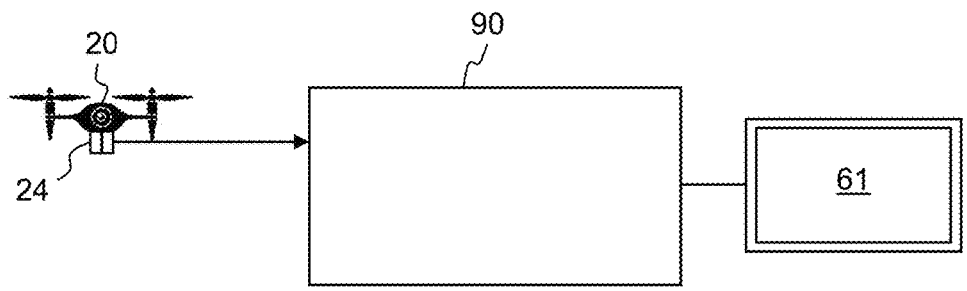
FIG. 9A is an overview of a system for rescue support.
Figure 9B:
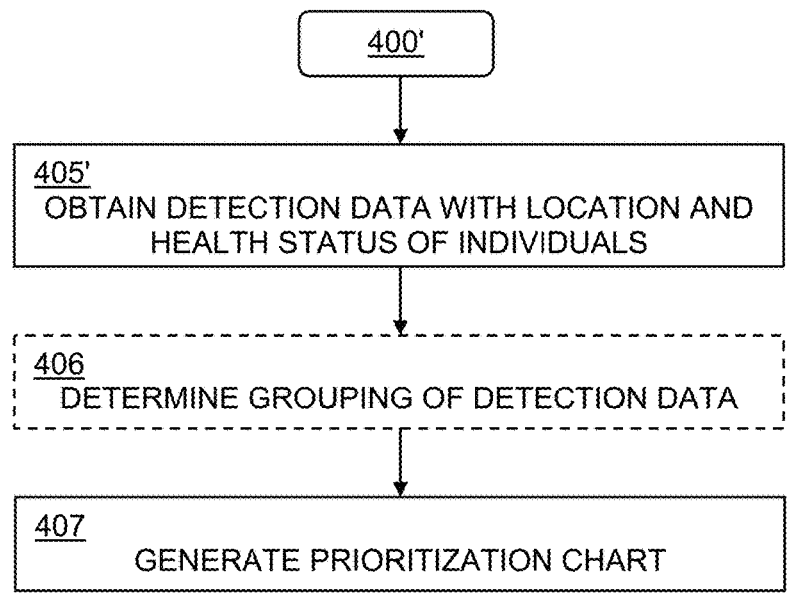
FIG. 9B is a flow chart of a method for rescue support.

The processing need not be distributed between the controller 21, the first processing device 40 and the second processing device 60 as described in the foregoing. Generally, as depicted in FIG. 9A, the system may be considered to include a computer system 90, which may encompass one or more of the controller 21, the first processing device 40 and the second processing device 60 and which may implement the method 400' represented by a flow chart in FIG. 9B. Step 405' obtains detection data that comprises one or more pairs of location and health status. Step 405' may obtain the detection data by processing one or more distress signals received by the signal receiver 24 on one or more drones 20, as shown in FIG. 9A, or by extracting one or more pairs of location and health status from the first data DD1 and/or the second data DD2 (FIG. 1). Steps 406-407 have been described with reference to FIG. 4 and will not be repeated.

Thus, the method 400' may be implemented on a single one of the controller 21, the first processing device 40 or the second processing device 60. To enable the controller 21 on a drone 20 to perform the method, the drones may be equipped for inter-drone communication that allows a master drone to receive detection data from slave drones, whereby the controller 21 on the master drone may generate the chart and transmit the chart to a remote display device, for example at a rescue coordination center.

Figure 9C:
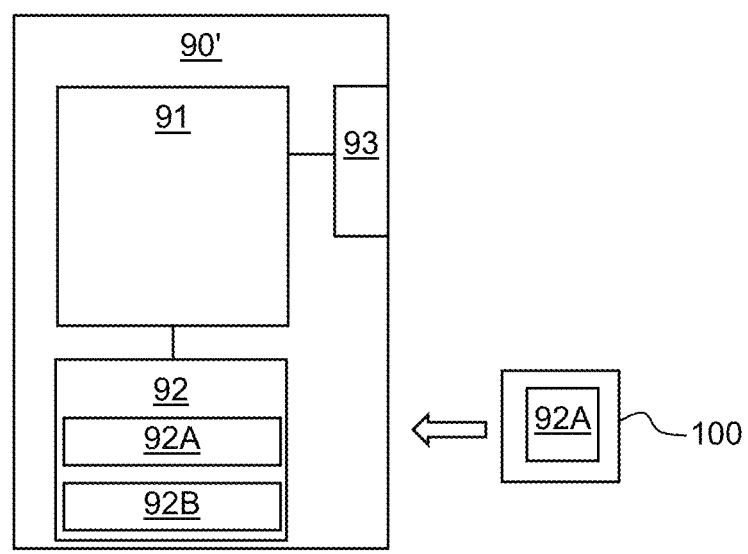
FIG. 9C is a block diagram of a computer system that is included in the system of FIG. 9A.

The computer system 90 may be implemented by hardware or a combination of software and hardware. In some embodiments, such hardware comprises one or more software-controlled computer resources. FIG. 9C schematically depicts such a computer resource 90', which comprises a processing system 91, computer memory 92, and a communication interface 93 for input and/or output of data. The processing system 91 may e.g. include one or more of a CPU ("Central Processing Unit"), a DSP ("Digital Signal Processor"), a microprocessor, a microcontroller, an ASIC ("Application-Specific Integrated Circuit"), a combination of discrete analog and/or digital components, or some other programmable logical device, such as an FPGA ("Field Programmable Gate Array"). A control program 92A comprising computer instructions is stored in the memory 92 and executed by the processing system 91 to perform any of the methods, operations, functions or steps described in the foregoing. As indicated in FIG. 9C, the memory 92 may also store control data 92B for use by the processing system 92. The control program 92A may be supplied to the computer resource 90' on a computer-readable medium 100, which may be a tangible (non-transitory) product (e.g. magnetic medium, optical disk, read-only memory, flash memory, etc.) or a propagating signal.

While the subject of the present disclosure has been described in connection with what is presently considered to be the most practical embodiments, it is to be understood that the subject of the present disclosure is not to be limited to the disclosed embodiments, but on the contrary, is intended to cover various modifications and equivalent arrangements included within the spirit and the scope of the appended claims.

In one alternative embodiment, the transponders 11 transmit the distress signals for receipt by one or more fixed or moveable transponder centrals in the geographic region. The respective transponder central may perform the processing of the distress signals in accordance with step 405 in FIG. 4 to determine location and health status and may then transmit corresponding detection data for receipt by one or more drones.

In one alternative embodiment, the transponders 11 may be configured for inter-transponder communication and arranged to autonomously form groups of transponders with a master transponder each. The master transponder may be configured to receive data on health status (and optionally location) from the other transponders in the group and generate a distress signal containing the data, as well as health status (and optionally location) of the master transponder. The role as master transponder may be rotated among the transponders in the group. This alternative embodiment may reduce the power consumption of the transponders as a whole.

In another alternative embodiment, the distress signal does not include a transponder identifier. Instead, the computer system 90 performs a statistical analysis of the combinations of location and health status derived from the intercepted distress signals to estimate the distribution of individuals in need of rescue within the geographical region.

Further, while operations are depicted in the drawings in a particular order, this should not be understood as requiring that such operations be performed in the particular order shown or in sequential order, or that all illustrated operations be performed, to achieve desirable results. In certain circumstances, parallel processing may be advantageous.

In the following, items are recited to summarize some aspects and embodiments as disclosed in the foregoing.

Item 1: A system for rescue support, comprising:
a fleet of unmanned aerial vehicles (20) for deployment within a geographic region, the unmanned aerial vehicles (20) being configured to receive distress signals (DS) transmitted by transponder devices (11) worn or carried by individuals in the geographic region subsequent to a large-scale emergency situation, and
a computer system (90) configured to:
process the distress signals to obtain detection data (DD) for the individuals, the detection data (DD) comprising a location of a respective transponder device among the transponder devices (11) and a health status of a respective individual among the individuals, and
generate, based on the location and health status, a prioritization chart (600) for the geographic region, the prioritization chart (600) being indicative of one or more sub-regions (P1, P2, P3) to be prioritized for a rescue operation.

Item 2: The system of item 1, wherein the distress signals (DS) comprise physiological data from one or more sensors (15) in or associated with the respective transponder (11), and wherein the computer system (90) is configured to: determine the health status of the respective individual as a function of the physiological data.

Item 3: The system of item 1 or 2, wherein the computer system is further configured to: determine a grouping of the detection data (DD) as a function of at least the location of the respective transponder device (11), wherein the prioritization chart (600) is generated based on the grouping.

Item 4: The system of item 3, wherein the computer system (90) is configured to: identify, based on the health status the respective individual, selected individuals among the individuals in the geographic region, and determine the grouping for the selected individuals.

Item 5: The system of item 3 or 4, wherein the grouping results in a plurality of groups of individuals, wherein the computer system (90) is configured to determine a density of individuals in a respective group among the plurality of groups, wherein the one or more sub-regions (P1-P3) comprises one or more groups with the highest density of individuals among the plurality of groups.

Item 6: The system of any preceding item, wherein the computer system (90), when processing the distress signals (DS), is configured to: extract an identifier in a respective distress signal among the distress signals and determine the location and the health status for each unique identifier.

Item 7: The system of any preceding item, wherein the computer system (90) is configured to: indicate locations of individuals or ensembles of individuals in the prioritization chart (600).

Item 8: The system of any preceding item, wherein the computer system (90) is configured to: generate, based on the health status in the detection data (DD), a count of living individuals in said one or more sub-regions (P1, P2, P3), and include the count in the prioritization chart (600).

Item 9: The system of any preceding item, wherein the computer system (90) is configured to: indicate, in the prioritization chart (600), a location of one or more rescue teams in relation to the geographic region.

Item 10: The system of any preceding item, wherein the computer system (90) is further configured to: receive rescue status data indicative of locations visited by one or more operative rescue teams, and indicate the locations visited on the prioritization chart (600).

Item 11: The system of any preceding item, wherein the unmanned aerial vehicles (20) comprise one or more environmental sensors (26) for generating environment data representative of surroundings of the fleet of unmanned aerial vehicles (20), wherein the computer system (90) is further configured to: generate the prioritization chart (600) based on the environment data.

Item 12: The system of item 11, wherein the one or more environmental sensors (26) comprise one or more of an imaging device, a temperature sensor, a pressure sensor, a sound detector, a weather sensor, a wind sensor, a humidity sensor, a dew point sensor, a substance sensor, or a radioactivity sensor.

Item 13: The system of item 11 or 12, wherein the computer system (90) is further configured to: determine the one or more sub-regions (P1, P2, P3) as a function of the environment data.

Item 14: The system of any one of items 11-13, wherein the computer system (90) is further configured to: include at least part of the environment data in the prioritization chart (600).

Item 15: The system of any one of items 11-14, wherein the environment data comprises one or more images, wherein the computer system (90) is further configured to: process the one or more images to determine an infrastructure status within the geographic region.

Item 16: The system of item 15, wherein the computer system (90) is further configured to: determine, based on the infrastructure status, an estimated time of arrival to the one or more sub-regions (P1, P2, P3) for one or more rescue teams located at a respective current location in relation to the geographic region, and include the estimated time of arrival in the prioritization chart (600).

Item 17: The system of item 15 or 16, wherein the computer system (90) is further configured to: select, based on the infrastructure status, one or more candidate rescue teams among a set of available rescue teams, and indicate the one or more candidate rescue teams in the prioritization chart (600).

Item 18: The system of any one of items 15-17, wherein the computer system (90) is further configured to select, based on the infrastructure status, a mode of transport among a set of available modes of transport for at least one rescue team, and indicate the mode of transport in the prioritization chart (600).

Item 19: The system of any one of items 15-18, wherein the computer system (90) is further configured to determine, based on the infrastructure status, a transportation route for a rescue team to the one or more sub-regions (P1, P2, P3), and indicate the transportation route in the prioritization chart (600).

Item 20: The system of any preceding item, wherein the computer system (90) is further configured to: provide, via the prioritization chart (600), access to a controller (21) of an unmanned aerial vehicle (20) in the fleet of unmanned aerial vehicles (20).

Item 21: The system of item 20, wherein the access to the controller (21) comprises an interface (CH) on the prioritization chart (600) for controlling the unmanned aerial vehicle to a selected location in the geographic region and/or an interface (602F) on the prioritization chart (600) for real-time access to an environmental sensor (26) on the unmanned aerial vehicle (20).

Item 22: The system of any preceding item, wherein the distress signals (DS) comprise at least one of a distance (D1, D2, D3) and a direction (a) from a respective unmanned aerial vehicle (20) to the respective transponder device (11), wherein the computer system (90) is configured to: generate the location of the respective transponder device (11) as a function of a current position of the respective unmanned aerial vehicle (20) and said at least one of a distance (D1, D2, D3) and a direction (a).

Item 23: The system of any preceding item, further comprising the transponder devices (11) which are configured to be worn or carried by the individuals and operable to transmit the distress signals, the transponder devices being further operable to measure one or more physiological parameters of the individuals and include the thus-measured one or more physiological parameter in the distress signals.

Item 24: The system of any preceding item, wherein the computer system (90) is further configured to: operating a display device (61) to present the prioritization chart (600).

Item 25: A computer-implemented method for rescue support, comprising:

obtaining (405') detection data representative of distress signals that are transmitted subsequent to a large-scale emergency situation by transponder devices worn or carried by individuals in a geographic region and received by unmanned aerial vehicles in a fleet of unmanned aerial vehicles deployed within the geographic region, the detection data comprising a location of a respective transponder device among the transponder devices and a health status of a respective individual among the individuals; and generating (407), based on the location of and health status, a prioritization chart for the geographic region, the prioritization chart being indicative of one or more sub-regions to be prioritized for a rescue operation.

Item 26: The method of item 25, wherein said obtaining (405') the detection data comprises: determining the health status of the respective individual as a function of physiological data included in the distress signals.

Item 27: A computer-readable medium comprising computer instructions (92A) which, when executed by a processing system (91), cause the processing system (91) to perform the method of item 25 or 26.

Item 28: A device comprising logic (91, 92) configured to control the device to perform the method of item 25 or 26.

Item 29: The device of item 28, which further comprises a signal receiver (24) for receiving the distress signals, wherein the logic (91, 92) is further configured to obtain at least part of the detection data (DD) by processing (405) one or more distress signals received by the signal receiver (24).

Item 30: The device of item 28 or 29, wherein the device is an unmanned aerial vehicle (20).

Item 31: A method for rescue support, comprising:
distributing (401) transponder devices to individuals in a geographic region;
causing (402) the transponder devices to be activated;
controlling (403) a fleet of unmanned aerial vehicles operable within the geographic region to receive distress signals transmitted by the transponder devices subsequent to a large-scale emergency situation in the geographic region, and
operating a computer system to:
process (405) the distress signals to obtain detection data for the individuals, the detection data comprising a location of a respective transponder device among the transponder devices and a health status of a respective individual among the individuals, and
generate (407), based on the location and health status of the respective individual, a prioritization chart for the geographic region, the prioritization chart being indicative of one or more sub-regions to be prioritized for a rescue operation.

The invention claimed is:

1. A system for rescue support, comprising:
a fleet of unmanned aerial vehicles for deployment within a geographic region, the unmanned aerial vehicles being configured to receive distress signals transmitted by transponder devices worn or carried by individuals in the geographic region subsequent to a large-scale emergency situation, wherein the distress signals include physiological data from one or more sensors associated respective transponder devices,
wherein at least one unmanned aerial vehicle of the fleet of unmanned aerial vehicles includes one or more environmental sensors for generating environment data representative of surroundings of the at least one unmanned aerial vehicle, the environment data includes one or more images; and
a computer system configured to:
process the distress signals to obtain detection data for the individuals, the detection data comprising a location of a respective transponder device among the transponder devices and a health status of a respective individual among the individuals, wherein the health status is determined based on the physiological data,
process the one or more images to determine an infrastructure status within the geographic region, and
generate, based on the location, health status, and environment data, a prioritization chart for the geographic region, the prioritization chart being indicative of one or more sub-regions with associated priorities for a rescue operation,
wherein to generate the prioritization chart, the computer system is further configured to perform one or more of:
determine an estimated time of arrival to the one or more sub-regions for one or more rescue teams located at a respective current location in relation to the geographic region, and include the estimated time of arrival in the prioritization chart;
select one or more candidate rescue teams among a set of available rescue teams, and indicate the one or more candidate rescue teams in the prioritization chart;
select a mode of transport among a set of available modes of transport for at least one rescue team, and indicate the mode of transport in the prioritization chart; or
determine a transportation route for a rescue team to the one or more sub-regions, and indicate the transportation route in the prioritization chart.

2. The system of claim 1, wherein the computer system is further configured to: determine a grouping of the detection data as a function of at least the location of the respective transponder device, wherein the prioritization chart is generated based on the grouping.

3. The system of claim 2, wherein the computer system is configured to:
identify, based on the health status the respective individual, selected individuals among the individuals in the geographic region, and determine the grouping for the selected individuals.

4. The system of claim 2, wherein the grouping results in a plurality of groups of individuals, wherein the computer system is configured to determine a density of individuals in a respective group among the plurality of groups, wherein the one or more sub-regions comprises one or more groups with the highest density of individuals among the plurality of groups.

5. The system of claim 1, wherein the computer system, when processing the distress signals, is configured to: extract an identifier in a respective distress signal among the distress signals and determine the location and the health status for each unique identifier.

6. The system of claim 1, wherein the computer system is configured to:
indicate locations of individuals or ensembles of individuals in the prioritization chart.

7. The system of claim 1, wherein the computer system is configured to:
generate, based on the detection data, a count of living individuals in said one or more sub-regions, and include the count in the prioritization chart.

8. The system of claim 1, wherein the computer system is configured to:
indicate, in the prioritization chart, a location of one or more rescue teams in relation to the geographic region.

9. The system of claim 1, wherein the computer system is further configured to: receive rescue status data indicative of locations visited by one or more operative rescue teams, and indicate the locations visited on the prioritization chart.

10. The system of claim 1, wherein the computer system is further configured to: determine the one or more sub-regions as a function of the environment data.

11. The system of claim 1, wherein the computer system is further configured to: provide, via the prioritization chart, access to a controller of an unmanned aerial vehicle in the fleet of unmanned aerial vehicles.

12. The system of claim 1, wherein the distress signals comprise at least one of a distance and a direction from a respective unmanned aerial vehicle to the respective transponder device, wherein the computer system is configured to: generate the location of the respective transponder device as a function of a current position of the respective unmanned aerial vehicle and said at least one of a distance and a direction.

13. The system of claim 1, further comprising the transponder devices which are configured to be worn or carried by the individuals and operable to transmit the distress signals, the transponder devices being further operable to measure one or more physiological parameters of the individuals and include the thus-measured one or more physiological parameter in the distress signals.

14. A computer-implemented method for rescue support, comprising:
obtaining detection data representative of distress signals that are transmitted subsequent to a large-scale emergency situation by transponder devices worn or carried by individuals in a geographic region and received by unmanned aerial vehicles in a fleet of unmanned aerial vehicles deployed within the geographic region, the distress signals include physiological data from one or more sensors associated with the respective transponders devices, the detection data comprising a location of a respective transponder device among the transponder devices and a health status of a respective individual among the individuals, wherein the health status is determined based on the physiological data;
obtaining environment data from at least one unmanned aerial vehicle of the fleet of unmanned aerial vehicles, wherein the at least one unmanned aerial vehicle includes one or more environmental sensors for generating environment data representative of surroundings of the at least one unmanned aerial vehicle, the environment data includes one or more images;
process the one or more images to determine an infrastructure status within the geographic region; and
generating, based on the location, health status, and environment data, a prioritization chart for the geographic region, the prioritization chart being indicative of one or more sub-regions with associated priorities for a rescue operation,
wherein generating the prioritization chart includes one or more of:
determining an estimated time of arrival to the one or more sub-regions for one or more rescue teams located at a respective current location in relation to the geographic region, and include the estimated time of arrival in the prioritization chart;
selecting one or more candidate rescue teams among a set of available rescue teams, and indicate the one or more candidate rescue teams in the prioritization chart;
selecting a mode of transport among a set of available modes of transport for at least one rescue team, and indicate the mode of transport in the prioritization chart; or
determining a transportation route for a rescue team to the one or more sub-regions, and indicate the transportation route in the prioritization chart.

15. A method for rescue support, comprising:
distributing transponder devices to individuals in a geographic region;
causing the transponder devices to be activated;
controlling a fleet of unmanned aerial vehicles operable within the geographic region to receive distress signals transmitted by the transponder devices subsequent to a large-scale emergency situation in the geographic region, wherein the distress signals include physiological data from one or more sensors associated respective transponder devices,
wherein at least one unmanned aerial vehicle of the fleet of unmanned aerial vehicles includes one or more environmental sensors for generating environment data representative of surroundings of the at least one unmanned aerial vehicle, the environment data includes one or more images; and
operating a computer system to:
process the distress signals to obtain detection data for the individuals, the detection data comprising a location of a respective transponder device among the transponder devices and a health status of a respective individual among the individuals, wherein the health status is determined based on the physiological data,
process the one or more images to determine an infrastructure status within the geographic region, and
generate, based on the location, health status of the respective individual, and environment data, a prioritization chart for the geographic region, the prioritization chart being indicative of one or more sub-regions with associated priorities for a rescue operation
wherein to generate the prioritization chart, the computer system is further configured to perform one or more of:
determine an estimated time of arrival to the one or more sub-regions for one or more rescue teams located at a respective current location in relation to the geographic region, and include the estimated time of arrival in the prioritization chart;
select one or more candidate rescue teams among a set of available rescue teams, and indicate the one or more candidate rescue teams in the prioritization chart;
select a mode of transport among a set of available modes of transport for at least one rescue team, and indicate the mode of transport in the prioritization chart; or
determine a transportation route for a rescue team to the one or more sub-regions, and indicate the transportation route in the prioritization chart.

* * * * *